United States Patent [19]

Kleppinger

[11] 4,001,952
[45] Jan. 11, 1977

[54] HYSTEROSCOPY TEACHING AID

[76] Inventor: Trygve M. Kleppinger, 1300 Lancaster Pike, Reading, Pa. 19607

[22] Filed: Oct. 24, 1975

[21] Appl. No.: 625,384

[52] U.S. Cl. .................................. 35/17; 269/323
[51] Int. Cl.² ..................... G09B 23/30; A61G 13/00
[58] Field of Search .............. 35/17; 269/322, 323, 269/328; 128/DIG. 15

[56] References Cited

UNITED STATES PATENTS

| | | | |
|---|---|---|---|
| 322,437 | 7/1885 | Gaston | 269/323 |
| 839,755 | 12/1906 | Harper | 269/323 |
| 2,345,489 | 3/1944 | Lord | 35/17 |
| 3,358,141 | 12/1967 | Hoffmann | 269/328 X |
| 3,650,523 | 3/1972 | Darby | 269/328 |

*Primary Examiner*—Harland S. Skogquist
*Attorney, Agent, or Firm*—Berman, Aisenberg & Platt

[57] ABSTRACT

An educational device for displaying an extirpated uterus consisting of a box-like base having a pivotally adjustable supporting table. The front wall of the base is notched out and the table has a notch in its front edge registering with the notch in the front wall. A sponge-like block is provided in the space adjacent the notches. The table is provided with securing straps connected to opposite side margins of the table to hold an excised uterus on the table for display.

14 Claims, 6 Drawing Figures

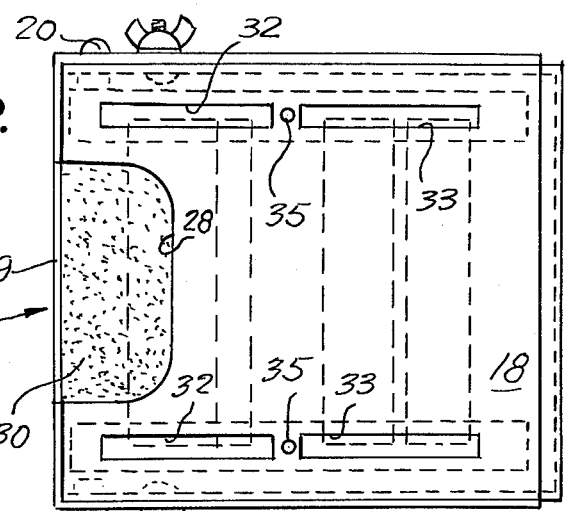
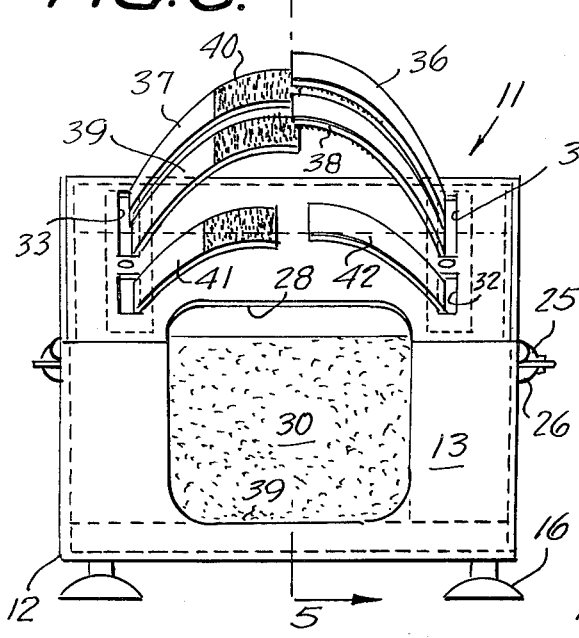
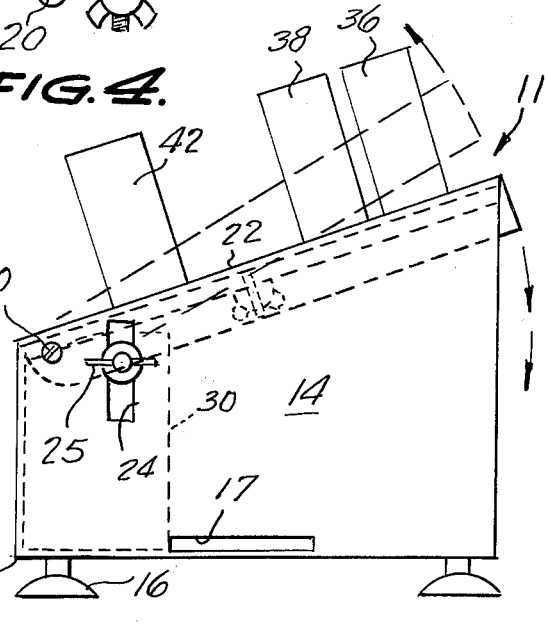
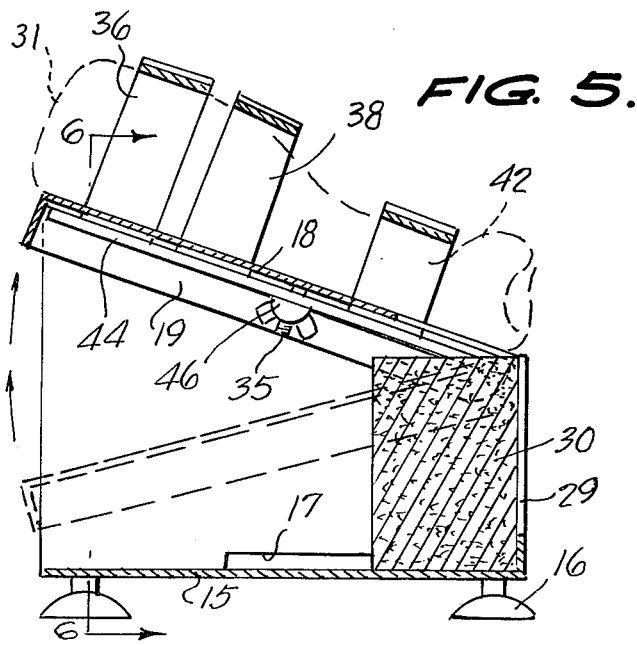

HYSTEROSCOPY TEACHING AID

This invention relates to educational devices, and more particularly to an anatomical display device for use in teaching the practice of hysteroscopy under non-operating room conditions and utilizing an extirpated uterine specimen.

A main object of the invention is to provide a novel and improved hysteroscopy teaching aid for facilitating the display of an extirpated uterine specimen for the purpose of providing instruction and demonstration of techniques associated with hysteroscopy (the visualization of the endometrial cavity of the uterus) under non-operating room conditions and utilizing an extirpated uterine specimen, the display device being very simple in construction, being easy to adjust so that the specimen is supported at various desired angles, and being valuable for teaching instruction and demonstration of the technique for transuterine sterilization by coagulation of the uterotubal ostia to medical students, interns, residents, obstetricians and gynecologists.

A further object of the invention is to provide an improved educational display device useful in teaching and demonstrating techniques associated with hysteroscopy, the device being inexpensive to fabricate, being compact in size, and being suitable for a wide range of techniques associated with gynecological practice, such as insertion of various intrauterine devices (I.U.D. devices and the like), menstrual extraction and/or aspiration, endometrial biopsy, cervical dilatation and curettage, uterine suction aspiration of eary intrauterine pregnancy, cervical cauterization, either thermal and/or cryosurgical, cervical biopsy, cervical conization, and colposcopy and colpomicrobiopsy.

A still further object of the invention is to provide an improved educational display device useful for teaching instruction and demonstration of the techniques associated with gynecological practice and which may also be used for the photography of the intrauterine cavity and endometrium during the various phases of the menstrual cycle and other submucosal pathological findings.

A still further object of the invention is to provide an improved display device for supporting an extirpated uterus and for adjusting same to various desired positions required for the demonstration of gynecological techniques or for the photography of portions of the extirpated uterus.

Further objects and advantages of the invention will become apparent from the following description and claims, and from the accompanying drawings, wherein:

FIG. 2 is a top plan view, to a semi-reduced scale, of the anatomical display device employed in FIG. 1.

FIG. 3 is a front elevational view of the display device of FIGS. 1 and 2.

FIG. 4 is a side elevational view of the display device of FIGS. 1 through 3.

FIG. 5 is a transverse vertical cross-sectional view taken substantially on line 5—5 of FIG. 3.

Figure 1:
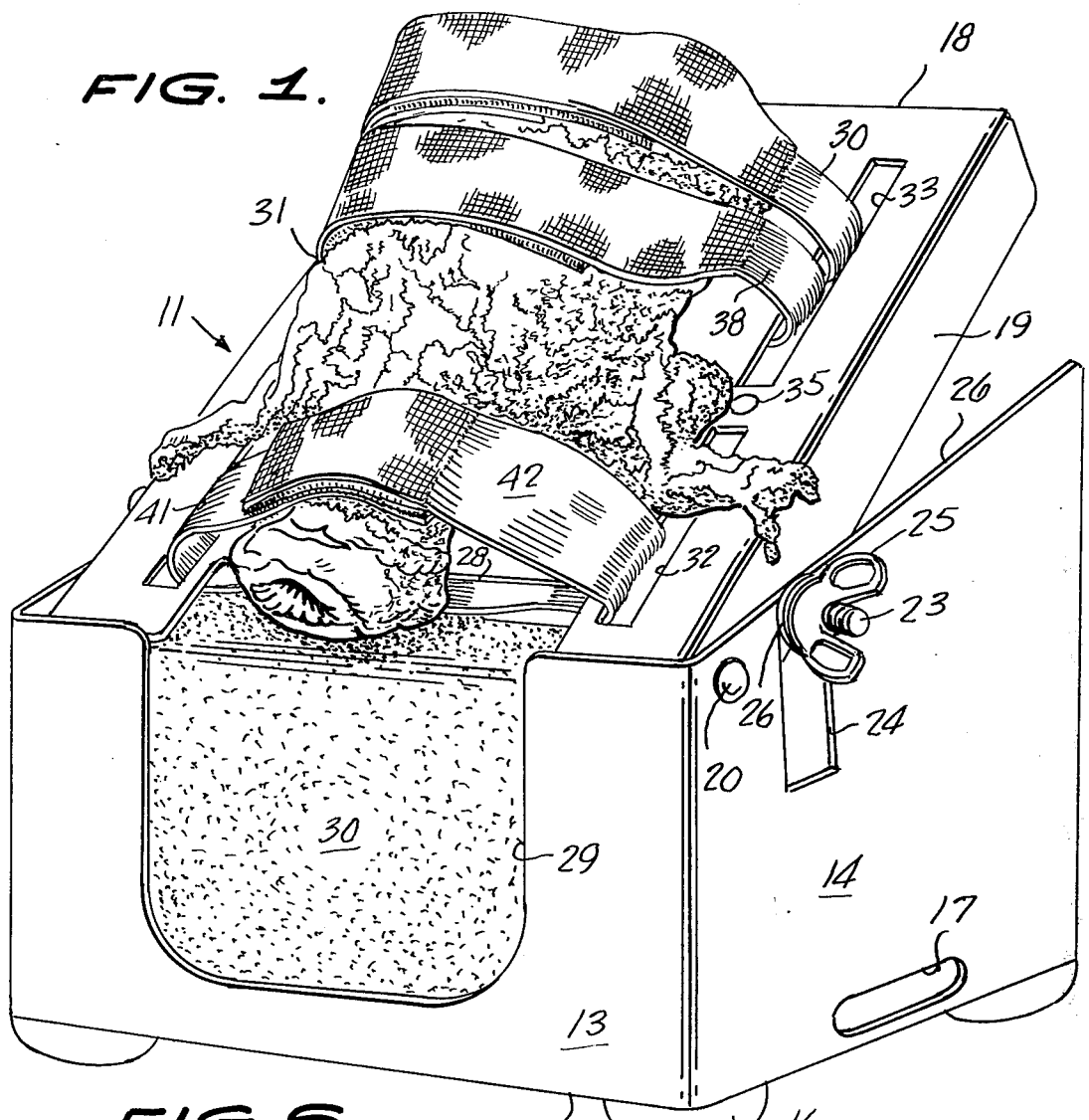
FIG. 1 is a perspective view of an improved anatomical display device according to the present invention, shown with an extirpated uterus mounted thereon and typically adjusted so that the uterus is in an inclined position.
Figure 6:
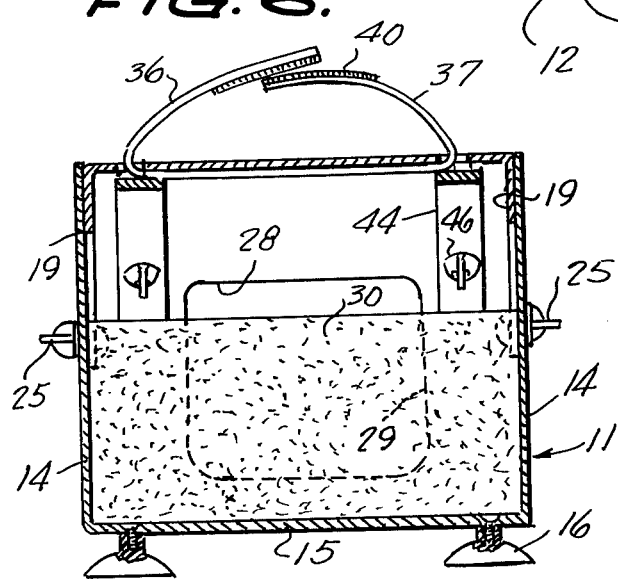
FIG. 6 is a vertical cross-sectional view taken substantially on line 6—6 of FIG. 5.

A prime purpose of the present invention is to provide a teaching aid primarily designed for the practice of hysteroscopy (the visualization of the endometrial cavity of the uterus) under non-operating room conditions and utilizing an extirpated uterine specimen. The important purposes of the display device include self-learning, teaching, instruction, and demonstration of the technique for transuterine sterilization by coagulation of the uterotubal ostia to medical students, interns, residents, obstetricians, and gynecologists.

A further aim of the present invention is to provide an apparatus which can be successfully employed in conjunction with the photography of the intrauterine cavity and endometrium during various phases of the menstrual cycle and other submucosal pathological conditions.

Ancillary intended uses of the anatomical display device of the present invention consist of the following:

For the teaching, instruction and demonstration of the proper technique for:

1. Insertion of the various intrauterine devices (I.U.D. devices and the like).
2. Menstrual extraction and/or aspiration.
3. Endometrial biopsy.
4. Cervical dilatation and curettage
5. Uterine suction aspiration of early intrauterine pregnancy.
6. Cervical cauterization, thermal and/or cryosurgical.
7. Cervical biopsy.
8. Cervical conization.
9. Colposcopy and colpomicrobiopsy.

Referring to the drawings, a typical anatomical teaching aid device according to the present invention is designated generally at 11. The device 11 comprises a box-like base 12 which has an upstanding front wall 13, upstanding side walls 14, 14 and a horizontal bottom wall 15. Secured to the bottom wall 15 adjacent the respective corners of the bottom wall are downwardly facing suction cups 16 for supportingly engaging the top surface of a suitable table, or alternatively, the base 12 may be fastened to a table by passing a fastening strap around the table top and through horizontal slots 17 provided at the intermediate lower portions of the side walls 14, 14.

Designated at 18 is a table member receivable in the top portion of the box-like base 12 and having depending side flanges 19, 19 received adjacent the inside surfaces of side walls 14, 14 and pivotally connected to the upper corner portions of the side walls by bolts 20, 20, as shown in FIGS. 2 and 4. The top edges of the side walls 14, 14 slope downwardly and forwardly as shown at 22, and the pivotal connections at 20, 20 are located so that the table member 18 may be rotated through a considerable angle, for example, may be rotated upwardly to an angle such as that shown in FIG. 1 wherein the table 18 is elevated above the top edges 22, 22 of the side walls 14, 14. Clamping means are provided for locking the table 18 in its adjusted position, comprising bolts 23, 23 engaged through the flanges 19, and passing through rectangular vertical slots 24 provided in the upper forward portions of the side walls 14, the bolts being provided with clamping wing nuts 25 which are clampingly engagable with the side walls 14, the slots 24 being of sufficient width to allow the necessary arcuate movement of the bolts 23 through the range of adjustment of table 18. The wing nuts 25 have relatively wide collar portions 26 so that they will engage the side marginal portions of the slots 24 in the various angularly adjusted positions of table 18.

The table member 18 is formed at its front margin with a relatively wide, generally U-shaped notch 28 of substantial depth, and the front wall 13 of base 12 is likewise formed with a relatively wide generally U-shaped opening 29 of substantial depth which is in registry with the table notch 28. A generally rectangular large foam sponge block 30 fills the front portion of the box-like base 12, extending adjacent the notches or openings 28, 29 and serving as a resilient support for the cervix portion of an extirpated uterus 31 mounted on the table 18 and secured thereto in a manner presently to be described.

The table member 18 is formed at each of its opposite side portions with a pair of elongated, generally rectangular slots 32 and 33 and is provided at said opposite side portions with respective clamping bars 44, 44 underlying the slots 32, 33 and secured thereto by bolts 35 extending through the bars 44 and the portions of the table member 18 between the slots 32, 33. Clamping wing nuts 46 are provided on the bolts 35 under the bars 44. Respective cooperating pairs of strap segments 36, 37 and 38, 39 are engaged through the rear slots 33, 33 and are clamped to the undersurface of the table member 18 by the clamping bars 44, 44. The straps are provided at their overlapping surfaces with Velcro pad portions 40 for fastening the overlapping portions of the straps together. It will be understood that in the typical case above illustrated, the straps 37, 39 have upwardly facing Velcro pads 40 and the straps 38, 36 have downwardly facing Velcro pad portions.

A similar pair of cooperating hold-down strap segments 41, 42 are engaged through the front slots 32, 32 for holding down the cervix portion of the extirpated uterus 31. As above-mentioned, the various straps are clampingly held by the clamping bars 44 when the clamping wing nuts 46 are tightened.

It will be understood that the strap segments 36, 37 and the other cooperating strap segments 38, 39 and 42, 41 may comprise the opposite end portions of continuous straps passed through the slots 33, 32 and extending beneath the bottom surface of the top wall of table 18. Appropriate adjustment of the length of the working end portions of the straps, in accordance with the size of the specimen to be clamped on the table, may be made by loosening the wing nuts 46, adjusting the end segments 36, 37, 38, 39 and 42, 41 to their desired lengths, and thereafter tightening the wing nuts 46.

The bolts 35 are rigidly secured to the table 18 in any suitable manner, for example, by being silver brazed to the undersurface of the table or stage 18.

The hold-down straps are preferably of the elastic type so that they will exert resilient gripping pressure on the specimen 31.

In using the device 11, an extirpated uterine specimen 31 is held in position on the table or stage 18 at its rear portion by the cooperation of the rear belt segments 36, 37 and 38, 39. As above-mentioned, the elastic strap segments 36, 37 and 38, 39 are adjustable in position on the stage in accordance with the side of the fundus of the uterus 31, so as to accommodate various sized uteri, and are likewise adjustable to allow for unimpeded insufflation of the uterus with $CO_2$ gas. The cervix portion of the uterus is held down on the sponge block 30 by the cooperating front elastic strap suctions 42, 41. The cervix portion of the uterus protrudes beyond the cutout portion 28 and rests on the top of the large foam sponge block 30 which fills the front portion of the box-like base 12. The cutout portions 28 and 29 are of substantial size and allow for the accommodation of a cervical adaptor to be applied to the cervix, thereby giving mobility to the adaptor and simulating female pelvic conditions. The stage or table 18 may be adjusted through a considerable angular range, for example, through an arc of approximately 75°, pivoting on the pivot bolts 20, as above-explained, thereby enabling simulation of many varied anatomical positions of the uterus 31, from anteflexion through retroversion. The stage or table 18 is positioned at the desired angle by loosening the wing nuts 25, moving the stage or table 18 to the desired angle, and finally tightening the wing nuts to maintain the position of the stage or table 18.

As above-mentioned, the device may be supported on the suction cups 16, or alternatively, may be anchored firmly to an examination table or other table by a wide flexible belt passing through the slots 17 and fastened around the table top.

While a specific embodiment of an improved hysteroscopy teaching aid device has been disclosed in the foregoing description, it will be understood that various modifications within the spirt of the invention may occur to those skilled in the art. Therefore, it is intended that no limitations be placed on the invention except as defined by the scope of the appended claims.

What is claimed is:

1. An anatomical display device comprising a box-like base having upstanding front and side walls, a stage member pivoted to the upper front corner portions of the side walls, means to clamp the stage member in pivotally adjusted position, and flexible strap means connected to opposite side marginal portions of the stage member for holding an anatomical specimen on the stage member.

2. The anatomical display device of claim 1 and wherein the front edge of the stage member and the front wall of the base are formed with registering relatively large notches and a resilient block is provided in the base adjacent the notches.

3. The anatomical display device of claim 2, and wherein the block comprises sponge material.

4. The anatomical display device of claim 3 and wherein said strap means comprises a plurality of spaced pairs of cooperating strap segments secured to the opposite side marginal portions of the stage member.

5. The anatomical display device of claim 4 and wherein the clamping means comprises laterally extending bolt elements, the side walls of the base having slots through which the bolt elements extend, and clamping nut members on the bolt elements clampingly engagable with the side walls.

6. The anatomical display device of claim 5 and wherein said slots extend substantially vertically.

7. The anatomical display device of claim 5, and wherein the stage member is formed at its opposite side marginal portions with slots through which the strap segments extend, and respective clamping plate members beneath the side marginal portions of said last-named slots clampingly engaging said strap segments.

8. The anatomical display device of claim 5, and wherein the strap segments comprise two pairs of cooperating strap segments at the rear portions of said stage member and a third pair of cooperating strap segments at the forward portion of said stage member.

9. The anatomical display device of claim 8 and wherein said stage member is formed at its rear side marginal portions with respective elongated slots to receive the two pairs of cooperating rear strap segments and is formed at its forward side marginal portions with additional elongated slots to receive the forward cooperating strap segments.

10. The anatomical display device of claim 9 and respective clamping plate members beneath the side marginal portions of the stage member, and fastening means extending through the clamping plate members and the portions of the stage member between the elongated slots to clamp the plate members against the strap segments.

11. An anatomical display device comprising a hollow base, an anatomical specimen support connected to said base, mating notches in said base and support cooperating to form an opening in said device, and means for holding an anatomical specimen on said support.

12. The device of claim 11, and a resilient support located in said base adjacent said opening.

13. The device of claim 11, and means for holding said specimen support in a selected pivoted position with respect to said base.

14. The device of claim 11, and wherein said specimen support is located within said base and pivotally connected thereto whereby said specimen support may be moved from its position within said base to a position extending out of said base.

* * * * *